United States Patent [19]

Vetter

[11] Patent Number: 5,080,649

[45] Date of Patent: * Jan. 14, 1992

[54] DUAL-COMPARTMENT HYPODERMIC SYRINGE

[75] Inventor: Udo J. Vetter, Ravensburg, Fed. Rep. of Germany

[73] Assignee: Arzneimittel GmbH Apotheker Vetter & Co. Ravensburg, Ravensburg, Fed. Rep. of Germany

[*] Notice: The portion of the term of this patent subsequent to Oct. 17, 2006 has been disclaimed.

[21] Appl. No.: 533,448

[22] Filed: Jun. 5, 1990

[30] Foreign Application Priority Data

Feb. 7, 1990 [EP] European Pat. Off. ...... 90 102373.9

[51] Int. Cl.$^5$ .................. A61M 37/00; A61M 5/08
[52] U.S. Cl. .................................. 604/91; 604/191; 604/208
[58] Field of Search ............ 604/82, 89, 90, 91, 604/187, 191, 207, 208, 210, 211, 224; 600/4.5; 222/136

[56] References Cited

U.S. PATENT DOCUMENTS

| | | | |
|---|---|---|---|
| 2,549,417 | 4/1951 | Brown | 604/90 |
| 2,591,046 | 4/1952 | Brown | 604/90 |
| 4,226,236 | 10/1980 | Genese | 604/89 |
| 4,312,343 | 6/1982 | LeVeen et al. | 604/211 |
| 4,583,974 | 4/1986 | Kokernak | 604/211 |
| 4,613,326 | 9/1986 | Szwarc | 604/89 |
| 4,792,329 | 12/1988 | Schreuder | 604/90 |
| 4,874,381 | 10/1989 | Vetter | 604/191 |
| 4,898,580 | 2/1990 | Crowley | 604/90 |
| 4,968,299 | 11/1990 | Ahlstrand et al. | 604/90 |
| 4,978,339 | 12/1990 | Labouze et al. | 604/110 |
| 4,994,043 | 2/1991 | Ysebaert | 604/191 |

Primary Examiner—C. Fred Rosenbaum
Assistant Examiner—Mark O. Polutta
Attorney, Agent, or Firm—Herbert Dubno; Andrew Wilford

[57] ABSTRACT

A hypodermic syringe has an elongated tubular body having a front end adapted to carry a needle, a rear end, and a bypass between the ends. A front partition piston defines with the front end a front compartment adapted to hold a substance and a rear piston defines with the front piston a rear compartment adapted to hold a fluid miscible with the front-compartment substance. The front piston is displaceable into a middle position in the bypass for fluid communication between the compartments. A stem projecting rearward out of the body from the rear piston is provided with axially spaced front and rear external screwthreads and has a clear region between the screwthreads. A damper on the rear end of the body can engage the screwthreads for slowing axial movement of the screwthreads past the rear end of the body and for permitting relatively rapid axial movement of the stem in the body when the clear region is level with the damper.

7 Claims, 1 Drawing Sheet

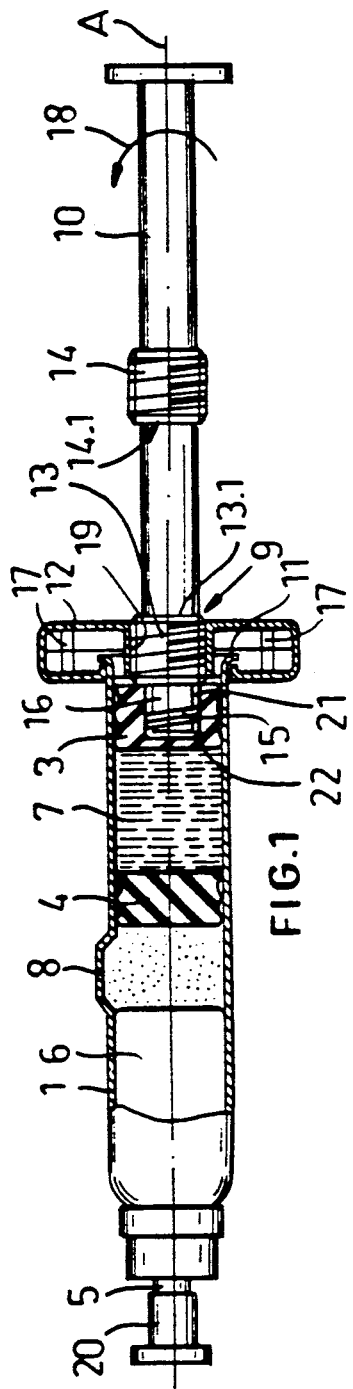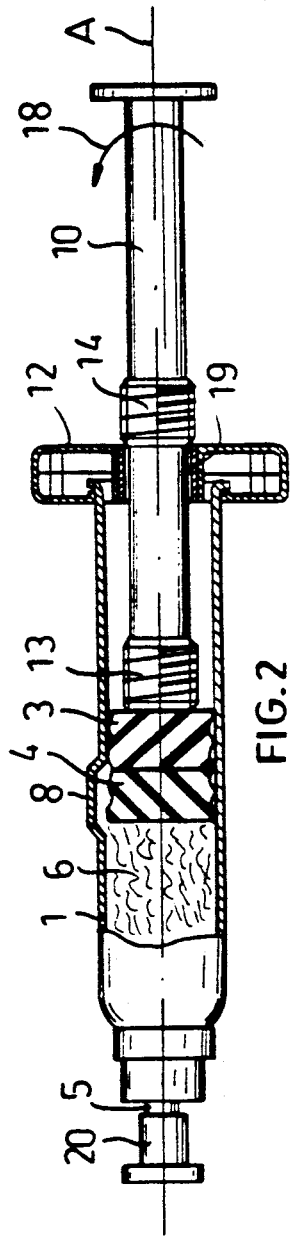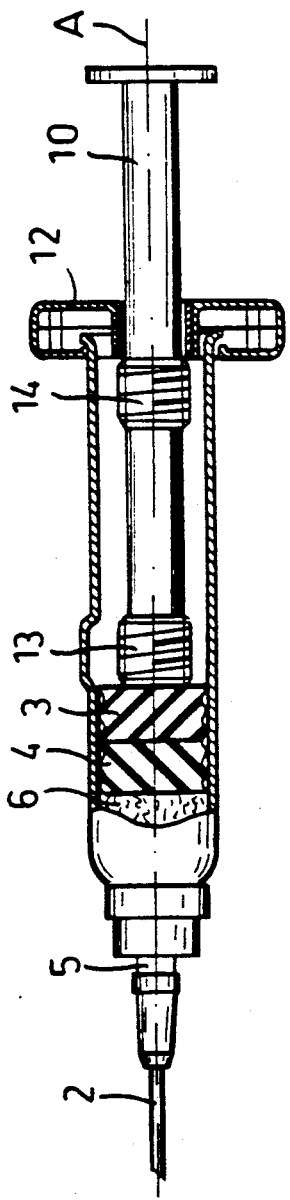

DUAL-COMPARTMENT HYPODERMIC SYRINGE

FIELD OF THE INVENTION

The present invention relates to a hypodermic syringe More particularly this invention concerns such a syringe set up to mix two substances prior to injecting same.

BACKGROUND OF THE INVENTION

A hypodermic syringe is described in my U.S. Pat. No. 4,874,381 which has a generally cylindrical syringe body centered on a longitudinal axis and formed with a front end having a needle-receiving fitting, a rear end opposite the front end, and a bypass intermediate the ends. A rear piston is slidable in the body proximal to the rear end and a front piston is slidable in the body between the rear piston and the front end. The pistons define in the syringe body a rear liquid compartment adapted to communicate with a front compartment between the front piston and the front end through the bypass upon displacement of the front piston so that opposite sides thereof are bridged by the bypass. A piston-actuating stem axially engaged by the rear piston extends out of the rear end and is axially displaceable to drive the pistons toward the front end of the body.

Similar such arrangements are describes in U.S. Pat. Nos. 2,591,046, 4,226,236, and 4,613,326. They allow the fluid in the rear compartment to be kept separate from a substance in the front compartment until they are needed. At that time the plunger is pushed longitudinally forward until the front partition piston aligns with the bypass and the fluid in the rear compartment is pumped past the now stationary front piston into the front compartment.

In my earlier patent damping is provided at the rear end of the body for restricting the velocity of the rear piston substantially until it reaches the bypass so as to limit the speed with which liquid from the liquid compartment enters the front compartment. The damping then disengages to permit faster axial displacement of the pistons by the stem. This damping is effected by a cap fitted onto the rear end and formed with a central bore having an internal screwthread. The stem has over part of its length an axially extending shank having an external screwthread threadedly engaging the internal screwthread and the shank has a length such that the external screwthread passes out of the internal screwthread upon rotation of the stem to advance the rear piston as the rear piston reaches the bypass. Thus for the first part of its stroke as the stem is pushed axially forward it must be slowly screwed through the cap on the syringe. Once the screwthread on the front portion of the stem disengages from the screwthread on the cap, which takes place roughly when the rear piston comes to rest against the rear face of the front piston, the screwthreads no longer limit forward advance of the stem for rapid ejection of the mixture in the front compartment.

Such an arrangement is excellent for easily mixed substances. When, however, the substance in the front compartment is, for example, a powder that does not readily go into suspension or solution with the liquid in the rear compartment, the above-described system provides no ready procedure for mixing. The user must shake the now ready syringe until the substance is fully mixed. If the mixture is incomplete it is possible for undissolved particles to block the needle or to remain in the syringe.

OBJECTS OF THE INVENTION

It is therefore an object of the present invention to provide an improved two-compartment hypodermic syringe.

Another object is the provision of such an improved two-compartment hypodermic syringe which overcomes the above-given disadvantages, that is which allows for thorough mixing of even relatively hard-to-combine substances.

A further object is an improved method of using such a syringe.

SUMMARY OF THE INVENTION

A hypodermic syringe according to this invention has an elongated tubular body having a front end adapted to carry a needle, a rear end, and a bypass between the ends. A front partition piston defines with the front end a front compartment adapted to hold a substance and a rear piston defines with the front piston a rear compartment adapted to hold a fluid miscible with the front-compartment substance The front piston is displaceable into a middle position in the bypass for fluid communication between the compartments A stem projecting rearward out of the body from the rear piston is provided with axially spaced front and rear stops and has a clear region between the stops. A damper on the rear end of the body can engage the stops for slowing axial movement of the stops past the rear end of the body and for permitting relatively rapid axial movement of the stem in the body when the clear region is level with the damper.

Such a syringe is used by first slowly advancing the front stop forward through the damper and thereby pushing the rear piston and front pistons forward until the front piston is level with the bypass. Thereafter the rear piston is rapidly advanced forward to force the fluid in the rear compartment axially forward in the bypass past the front piston into the front compartment so that the fluid of the rear compartment mixes with the substance of the front compartment. The rear piston is then rapidly retracted backward to draw the mixture from the front compartment through the bypass past the front piston into the rear compartment and then this piston is rapidly advanced forward to force the mixture in the rear compartment through the bypass past the front piston into the front compartment. These last two steps are repeated until the substance and fluid are thoroughly mixed. Then the rear stop is slowly advanced forward through the damper to push the pistons both forward until the front piston is forward of the bypass. The pistons are finally rapidly advanced forward to eject the mixture from the front compartment through the front end of the body.

With this arrangement, therefore, even relatively hard-to-mix substances can be surely combined. The violence of forcing the substance, typically a powder, and the fluid, typically a liquid, through the narrow bypass creates an intense mixing effect that can be repeated as much as necessary until full mixing is complete. The syringe is normally transparent so the user can verify how well its contents are mixed. The rear stop prevents the pistons from being advanced so far forward that the front piston is pushed forward of the bypass, ending the mixing action.

According to another feature of this invention the stops are respective axially short front and rear external screwthreads formed on the stem. The damper is a complementary internal screwthread provided at the rear body end. In addition the body is provided with a rear end cap formed with the internal screwthread. This cap has a pair of parts one of which is formed with the internal screwthread. The rear body end is formed with an outwardly projecting rim and the cap engages over this rim.

In accordance with a further invention feature the stem has a front end projection having a front portion formed with an external screwthread and a rear unthreaded portion The rear piston is formed with a rearwardly open pocket having a rear portion formed with an internal screwthread complementary to the external screwthread of the projection and an unthreaded front portion. Thus the screwthread of the projection can be screwed through the screwthread of the pocket to axially but not rotationally couple the stem and rear piston This makes it possible to package the stem separate from the rest of the syringe, but in no way makes assembling or using the syringe difficult.

DESCRIPTION OF THE DRAWING

The above and other objects, features, and advantages will become more readily apparent from the following, reference being made to the accompanying drawing in which:

FIG. 1 is a side view partly in axial section through a syringe according to this invention before use;

FIG. 2 is a view like FIG. 1 but showing the syringe in the mixing position; and FIG. 3 is a view like FIG. 1 but showing the syringe in the ready-to-use position.

SPECIFIC DESCRIPTION

As seen in FIG. 1 a syringe according to this invention has a basically cylindrical transparent glass or plastic body 1 centered on an axis A and having a front end 5 adapted to receive either a cap 20 or a needle 2 (FIG. 3), and a rear end formed with an outwardly projecting rim 11. A rear piston 3 and a front piston 4 define in the body 1 a front compartment 6 typically filled with a medicament powder and a rear compartment 7 filled with a liquid miscible with the front-compartment powder. The wall of the syringe body 1 is formed centrally with a bypass 8 basically constituted as an outwardly projecting and axially extending ridge defining an inwardly open and axially extending groove of an axial length slightly greater than that of the front piston 4.

An axially centered and elongated stem 10 projects rearwardly out of the cylinder 1 and has a front end formed as a small-diameter projection or stud 16 in turn having at its front portion a short screwthread 15. The rear piston 3 is formed with a rearwardly open blind pocket or recess 22 receiving this stud 16 and in turn having a rear portion formed with a short screw-thread 21 complementary to the screwthread 15. Thus the plunger stem 10 can be screwed into the back of the piston 3 but, once the screwthread 15 is screwed completely through the screwthread 16, the stem 10 will be axially coupled to the piston 3 but able to rotate freely about the axis A relative thereto as indicated by arrow 18.

According to this invention the rear end of the cylinder 1 is provided with a damper 9 in part constituted by a crosspiece 12 engaged over the rim 11 and formed with an internal screwthread 19. This crosspiece 12 can be made of two pieces held together axially by rivets 17 or can be made of two pieces hinged together about an axis parallel to the axis A. The stem 10 itself is formed with a pair of axially spaced threaded regions 13 and 14 complementary to the screwthread 19. Between a rear end 13.1 of the front thread 13 and a front end 14.1 of the rear thread 14 the stem 10 is unthreaded.

The above-described unit is used as follows:

The package is typically delivered to the user with the syringe body 1 provided with the cap 20 and with its internal parts in the position of FIG. 1, except that the stem 10 is not mounted in place. The stem 10 and needle 2 are separate.

For use the stem 10 is screwed simultaneously into the rear of the piston 2 and into the crosspiece 13. Typically the stem 10 is rotated as indicated by arrow 18 until slight forward movement of the pistons 3 and 4 is noted, as the fluid in the compartment 7 is normally incompressible. This leaves the structure in the position of FIG. 1 in which it is quite stable and inadvertent depression of the plunger 10 is impossible.

Then to mix the ingredients in the compartments 6 and 7, the stem 10 is further rotated until the screwthread 13 passes the crosspiece or cap 12, that is until its rear end 13.1 moves axially forward past the front end of the screwthread 19. This rotation of the stem 10, which will not be accompanied by a rotation of the piston 3 because the screwthreads 15 and 21 are out of engagement, will move both pistons 3 and 4 forward until the piston 4 is centered axially in the bypass 8 so that the two compartments 6 and 7 are in communication.

Subsequently as seen in FIG. 2 the stem 10 can be pushed axially forward, without rotation, until the front edge 14.1 of the rear screwthread 14 comes against the rear end of the crosspiece 12. This action will push the piston 4 forward until it abuts the rear face of the piston 3 and will pump the contents of the compartment 7 through the bypass 8 into the front compartment 6. The contents of the two compartments will therefore mix.

According to the invention it is thereafter possible to move the stem 10 and piston 3 back and forth axially between end positions defined by the abutments constituted by the ends 13.1 and 14.1 so as to pump the liquid back and forth between the compartments 6 and 7. This action will very thoroughly combine even relatively hard-to-mix substances Even though the mixing action is intense, there is no possibility of the contents being discharged because the forward position of the rear piston 3 is limited by the rear stop 14.1 to a position lying against the front piston 4 which itself is in the middle of the bypass 8.

Thereafter, once the contents of the syringe are fully mixed, the user replaces the cap 20 with the needle 2 and again rotates the stem 10 in direction 18 to screw the rear screwthread 14 through the end cap 12. This advances both pistons 3 and 4 axially forward, at least pushing the front piston 4 forward past the bypass 8. During such movement the needle 2 is held up so that air is driven out of the syringe.

Once the screwthread 14 is axially forward of the screwthread 19 of the crosspiece 12, the stem 10 can again be pushed forward to eject the mixed contents and inject them into the patient.

I claim:

1. A hypodermic syringe comprising:

an elongated tubular body centered generally on an axis and having
  a front end adapted to carry a needle,
  a rear end spaced axially behind the front end, and
  a bypass between the ends;
a front partition piston defining with the front end a front compartment adapted to hold a substance;
a rear piston defining with the front piston a rear compartment adapted to hold a fluid miscible with the front-compartment substance, the front piston being displaceable into a middle position in the bypass for fluid communication between the compartments;
a stem projecting axially rearward out of the body form the rear piston and provided with axially spaced front and rear stops and having a clear region between the stops; and
damper means on the rear end of the body engageable with the stops for slowing axial movement of the stops past the rear end of the body and permitting relatively rapid axial movement of the stem in the body when the stops axially flank the damper means and the clear region is level with the damper means.

2. The syringe defined in claim 1 wherein the stops are respective axially short front and rear external screwthreads formed on the stem, the damper means being a complementary internal screwthread provided at the rear body end.

3. The syringe defined in claim 2 wherein the body is provided with a rear end cap formed with the internal screwthread.

4. The syringe defined in claim 3 wherein the rear body end is formed with an outwardly projecting rim, the cap engaging over the rim.

5. The syringe defined in claim 1 wherein the stem has a front end projection having a front portion formed with an external screwthread and a rear unthreaded portion, the rear piston formed with a rearwardly open pocket having a rear portion formed with an internal screwthread complementary to the external screwthread of the projection and an unthreaded front portion, whereby the screwthread of the projection ca be screwed through the screwthread of the pocket to axially but not rotationally couple the stem and rear piston.

6. A hypodermic syringe comprising:
  an elongated tubular body having a front end adapted to carry a needle, a rear end, and a bypass between the ends;
  a front partition piston defining with the front end a front compartment adapted to hold a substance;
  a rear piston defining with the front piston a rear compartment adapted to hold a fluid miscible with the front-compartment substance, the front piston being displaceable into a middle position in the bypass for fluid communication between the compartments;
  a stem projecting rearward out of the body from the rear piston and provided with axially spaced front and rear external screwthreads and having an unthreaded region between the screwthreads; and
  means including an internal screwthread on the rear end of the body engaging the stops for slowing axial movement of the external screwthreads past the rear end of the body and for permitting relatively rapid axial movement of the stem in the body when the unthreaded region is level with the damper.

7. A method of using a hypodermic syringe comprising:
  an elongated tubular body having a front end adapted to carry a needle, a rear end, and a bypass between the ends;
  a front partition piston defining with the front end a front compartment adapted to hold a substance;
  a rear piston defining with the front piston a rear compartment adapted to hold a fluid miscible with the front-compartment substance, the front piston being displaceable into a middle position in the bypass for fluid communication between the compartments;
  a stem projecting rearward out of the body from the rear piston and provided with axially spaced front and rear stops and having a clear region between the stops; and
  means including a damper on the rear end of the body engaging the stops for slowing axial movement of the stops past the rear end of the body and for permitting relatively rapid axial movement of the stem in the body when the clear region is level with the damper; the method comprising the steps of sequentially:
  a) slowly advancing the front stop forward through the damper and thereby pushing the rear piston and front pistons forward until the front piston is level with the bypass;
  b) rapidly advancing the rear piston forward to force the fluid in the rear compartment axially forward in the bypass past the front piston into the front compartment, whereby the fluid of the rear compartment mixes with the substance of the front compartment;
  c) rapidly retracting the rear piston backward to draw the mixture from the front compartment through the bypass past the front piston into the rear compartment;
  d) rapidly advancing the rear piston forward to force the mixture in the rear compartment through the bypass past the front piston into the front compartment;
  e) repeating steps c) and d) until the substance and fluid are thoroughly mixed;
  f) slowly advancing the rear stop forward through the damper and thereby pushing the pistons both forward until the front piston is forward of the bypass; and
  g) rapidly advancing the pistons forward and ejecting the mixture from the front compartment through the front end of the body.

* * * * *